(12) United States Patent
Rouffet

(10) Patent No.: US 8,213,863 B2
(45) Date of Patent: Jul. 3, 2012

(54) METHOD FOR OPENING COMMUNICATION SESSIONS FOR REMOTE CONTROL BY A RADIO TERMINAL OF THE DISPLAY OF INFORMATION ON A SCREEN, AND ASSOCIATED SERVER

(75) Inventor: Denis Rouffet, Velizy (FR)

(73) Assignee: Alcatel Lucent, Paris (FR)

( * ) Notice: Subject to any disclaimer, the term of this patent is extended or adjusted under 35 U.S.C. 154(b) by 386 days.

(21) Appl. No.: 12/392,643

(22) Filed: Feb. 25, 2009

(65) Prior Publication Data

US 2009/0227207 A1 Sep. 10, 2009

(30) Foreign Application Priority Data

Feb. 25, 2008 (FR) ...................................... 08 51173

(51) Int. Cl.
*G06F 17/60* (2006.01)
(52) U.S. Cl. ................. 455/41.2; 709/217; 705/2; 705/5
(58) Field of Classification Search ................ 455/41–2; 709/217–219, 227–229; 705/2, 5, 10, 14.66, 705/26, 26.1, 26.7, 44
See application file for complete search history.

(56) References Cited

U.S. PATENT DOCUMENTS

| | | | |
|---|---|---|---|
| 2002/0159088 A1 | 10/2002 | Yamakawa et al. | |
| 2003/0149601 A1* | 8/2003 | Cabral ............................. | 705/5 |
| 2004/0019564 A1* | 1/2004 | Goldthwaite et al. .......... | 705/44 |
| 2004/0068439 A1 | 4/2004 | Elgrably | |
| 2006/0271445 A1* | 11/2006 | Lee et al. ........................ | 705/26 |
| 2008/0262871 A1* | 10/2008 | Lee et al. ........................ | 705/2 |
| 2009/0018898 A1* | 1/2009 | Genen ............................ | 705/10 |
| 2010/0299212 A1* | 11/2010 | Graylin et al. ............. | 705/14.66 |

FOREIGN PATENT DOCUMENTS

| | | |
|---|---|---|
| KR | 2003-0063674 | 7/2003 |
| KR | 2007-0050025 | 5/2007 |
| WO | WO 2006/049424 | 5/2006 |

OTHER PUBLICATIONS

French Search Report.

* cited by examiner

*Primary Examiner* — Vibol Tan
(74) *Attorney, Agent, or Firm* — Fay Sharpe LLP

(57) ABSTRACT

A method is dedicated to the opening of a communication session between a radio terminal (MS), connected to a radio network (R1) and a fixed communication terminal (TC), coupled to at least one target screen (EC) and connected to a communication network (R2). This method consists in sending, by means of the radio terminal (MS), an identifier displayed on the target screen (EC) to open a communication session between the said radio terminal (MS) and the fixed communication terminal (TC), and then to control display of the information on the target screen (EC) by means of the radio terminal (MS).

27 Claims, 2 Drawing Sheets

METHOD FOR OPENING COMMUNICATION SESSIONS FOR REMOTE CONTROL BY A RADIO TERMINAL OF THE DISPLAY OF INFORMATION ON A SCREEN, AND ASSOCIATED SERVER

FIELD OF THE INVENTION

The invention concerns the domain of the provision of information to individuals.

BACKGROUND OF THE INVENTION

It frequently happens that a person searches for information while traveling, for example in a city, a building, a public transport vehicle, or in a public place, or else while watching a television program. Several solutions are already known for this problem.

Thus, a person can for example use his/her mobile (or cellular) phone—or another type of radiocommunication terminal) to call a telephone information service or to gain access to an Internet information site.

Another solution consists in making available to people information stored in computers (or information technology terminals) coupled to interactive screens equipped (or combined) with a man/machine interface for selection and navigation (e.g. command keys (that may be tactile (touch sensitive areas on the screen)) and/or a mouse).

Another solution consists in positioning oneself close to a radio IT terminal (e.g. of the Bluetooth or Wi-Fi [W-LAN] type) in order to download onto a mobile phone (or any other type of radiotelecommunications terminal) suitable for such purposes information stored in the said terminal.

Yet another solution consists in photographing a cryptogram located on a poster or panel by means of the photo camera integrated in a mobile telephone (or any other type of radiotelecommunications terminal), so as to feed this into an internal services application capable of establishing a communication with a service server in order to communicate the photographed cryptogram to it for transmission of the pertinent information to the mobile phone.

A further solution consists in using panels on which information regularly scrolls by. However, it is not possible to interact with such panels, and therefore the person reading the panel is forced to wait for the information that is of interest to scroll by, and he/she also has no means to stop the scrolling or to reverse its direction to go back.

Yet another solution consists in implementing, for a mobile telephone (or any other type of radiotelecommunications terminal), an LBS [Location Based Service] type application in order to locate that mobile phone and transmit to it information concerning the place where it is located. This solution is, in particular, used in the applications enabling the downloading POIs, or Points of Interest in order to show them on a map.

Each of the above solutions has at least one disadvantage that renders it difficult to use by most people and/or, alternatively, not sufficiently user-friendly and/or informative.

SUMMARY OF THE INVENTION

The purpose of the invention is to propose an alternative solution to the solutions known from the prior art.

For this purpose, it proposes a method dedicated to the opening of a communication session between a radio (communication) terminal, connected to a radio (communication) network and a fixed communication terminal, coupled to at least one target screen and connected to a communication network (that may be the same as the radio network).

This method is characterized in that it consists in:
sending, by means of the radio terminal, an identifier (if applicable, a communication identifier) displayed on the target screen in order to open a communication session between that radio terminal and the fixed communication terminal, then
controlling the information display on the target screen by means of the radio terminal.

The method of the invention may comprise other characteristics, which may be taken separately or in combination, in particular:
the option to transfer control of the information display to the radio terminal:
it is possible to send to a server, by means of the radio terminal, an identifier chosen from a list displayed on the target screen; it is then possible to open the communication session by means of that server, and to proceed to the transfer of the display control by means of that server;
it is possible to dial the identifier with the radio terminal when it is a communication identifier;
it is possible to use means in the radio terminal (constituting a man/machine interface) to carry out operations enabling action on at least some of the information displayed on the target screen and/or to cause display on the target screen of certain stored information;
in the event of display on the target screen of information accompanied by another identifier granting access to other stored information, it is possible to cause display of such stored information by sending (if appropriate, by dialing) such other identifier via the radio terminal;
it is possible to display on a display screen of the radio terminal at least some of the information displayed on the target screen;
it is possible to initiate at least one telecommunications application, such as e.g. a connection application or an application enabling storage of at least some of the information displayed on the target screen within the storage means designated by the user of the radio terminal;
it is possible to transmit to the radio terminal audio messages associated to the information displayed to enable them to be heard by their user (and, if applicable, store these audio messages in the radio terminal);
the communication session can be terminated in the event of detection of an absence of display control operations with the radio terminal for a duration that is longer than a chosen threshold;
it is possible to terminate the communication session if the radio terminal user interrupts the communication;
it is possible to bill the user of the radio terminal for the control of the display;
it is possible to store in the fixed communication terminal at least some of the information intended to be displayed on the target screen;
it is possible to store in the server at least some of the information intended to be displayed on the target screen.

The invention also proposes a communication network server in charge in the event of establishment of a communication with a radio (communication) terminal connected to a radio (communication) network consecutively to the transmission by that radio terminal of an identifier displayed on a target screen coupled to a fixed communication terminal connected to a communication network in order to open a communication session between the radio terminal and the fixed communication terminal, and then to transfer to that radio terminal the control of the display of information on the target screen.

The server according to the invention may comprise other characteristics, which may be taken separately or in combination, in particular:

- it may be in charge, in the event of transmission (or potentially, of dialing) by the radio terminal during the communication session of another identifier displayed on the target screen and granting access to other stored information, of authorizing access to such other information stored in a manner such that it can be displayed on the target screen;
- it may be in charge of authorizing transmission to the radio terminal of at least some of the information displayed on the target screen with a view to its display on the display screen of the said radio terminal;
- an application serving to connect the user of the radio terminal with another user or with a telecommunications device such as e.g. an answering machine or a content server), or else an application enabling storage of at least some of the information displayed on the target screen within the storage means designated by the user of the radio terminal;
- it may be in charge of transmitting to the radio terminal audio messages associated to the information displayed to enable them to be heard by their user (and, if applicable, storing them locally);
- it may be in charge of terminating the communication session in the event of detection of an absence of display control operations with the radio terminal for a duration that is longer than a chosen threshold;
- it may be in charge of terminating the communication session if the radio terminal user interrupts the communication;
- it may be in charge of controlling the billing to the user of the radio terminal for the control of the display;
- it may comprise storage means storing at least some of the information intended to be displayed on the target screen;
- it may be in charge of authorizing transmission to an address designated by the user of the radio terminal of at least some of the information displayed on the target screen with a view to its storage in means of storage.

Other characteristics and advantages of the invention will become apparent upon examining the detailed description below, and the attached drawings, in which:

The attached drawings may serve not only to complete the invention, but also to contribute to its definition as necessary.

DETAILED DESCRIPTION OF THE INVENTION

The invention has as its objective, in particular, to enable availability of information on a so-called "target" screen coupled to (or constituting a part of) a fixed communication terminal connected to a communication network (wireline or wireless), for a person placed in front of that target screen and equipped with a (mobile or portable) radio communication terminal connected to a (wireless) radio communication network.

Figure 1:
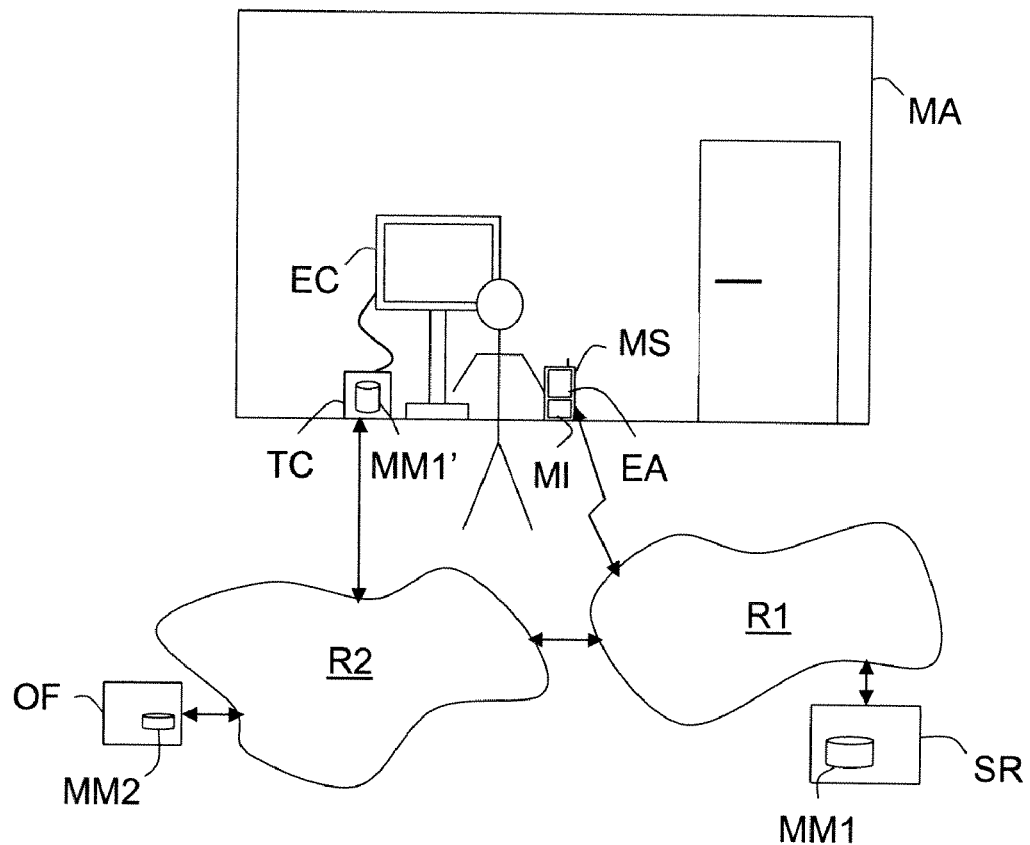
FIG. 1 highly schematically illustrates a shop window behind which is installed a target screen connected to a wireline communication terminal connected to a wireline network, and in front of which there is, temporarily, a person equipped with a mobile phone suitable for establishing a connection with a mobile network to which is connected a server according to the invention, FIG. 2 highly schematically illustrates an example of general information displayed on a target screen, FIG. 3 highly schematically illustrates an example of a group of eight information windows and/or icons, symbolizing keys to be activated to access the different information windows, and of a second communication identifier enabling access to other information displayed on a target screen after control is taken of its display, and FIG. 4 highly schematically illustrates an example of a group of three information windows displayed on a target screen after the second communication identifier is dialed.

Reference is made to FIG. 1 to present the invention by way of example and not of limitation.

In the example illustrated, a target screen EC is connected to a fixed communication terminal TC, itself connected to a communication network R2 (wireline or wireless), and both are installed in a shop window MA in front of which is momentarily situated a person equipped with a (mobile or portable) radio communication terminal MS capable of connection to a (wireless) radio communication R1 connected (directly or indirectly) to the communication network R2.

In the following discussion it is considered by way of example and not of limitation that the communication network R2 to which is connected the fixed communication terminal TC is different from the radio communication network to which is connected the (mobile or portable) radio communication terminal MS. However, this is not mandatory. In fact, the radio communication network may be one and the same.

Moreover, in the following discussion it is considered by way of example and not of limitation that the communication network R2 to which is connected the fixed communication terminal TC is a wireline network, e.g. of the ADSL type (potentially offering an IP access). However, a fixed communication terminal TC can be connected to other types of communication network, and more particularly a wireline network such as a cable or fiber optic network, or a wireless network, such as a mobile (or cellular) network, a local network (WLAN standards (including WiFi) and WiMAX)), a satellite network (for example in conformity with a DVB or similar standard) or a hybrid network. It can also be connected to several means of communication at once, thus enabling reception, e.g., on the one hand, of common information through e.g. a satellite broadcast network, and, on the other hand, of user dedicated information after taking control of the display e.g. by means of an ADSL network.

Furthermore, in the following discussion it is considered by way of example and not of limitation that the radio communication network R1 to which is connected the radio communication terminal MS is a wireless network, e.g. of the mobile (or cellular) type. potentially offering an IP access. In a general manner, the radio communication terminal MS can be connected to any type of radio network, and more particularly to a mobile (or cellular) network (GSM, CDMA, WCDMA, 3G LTE, or their further developments) or to a local network (WLAN (including WiFi) and WiMAX) standard), or else to a satellite network.

In addition, in the following discussion it is considered by way of example and not of limitation that the fixed communication terminal TC is a modem connected to at least one so-called target screen EC, and that the (mobile or portable) radio communication terminal MS is a mobile (or cellular)

telephone having a display screen EA and a man/machine interface Ml to input operation or action commands. However, the invention is not limited to these types of communication terminals. Indeed, the fixed communication terminal TC can also be a desktop (or potentially laptop) computer, a digital television set (or screen) equipped with (or comprising) a modem, or a content receiver equipped with a wireline or wireless communication module and potentially associated to a projector, and the (mobile or portable) radio communication terminal MS may equally be a personal digital assistant or PDA, including a "pocket PC" or a laptop computer (though this may not be very practical), or any further development of the abovementioned types.

It will be noted in particular that the radio communication terminal MS may also be a device equipped with a GPS receiver (whether or not removable) installed in a vehicle and enabling the opening of communication sessions by the fact that it comprises an integrated wireless communication module or that it is able to communicate with an external portable type communication module such as a Bluetooth connection. This makes it possible to use the invention on board a vehicle stopped in front of a target screen EC, and for example to implement an application for the indication and reservation of parking spaces before entering the parking lot, and to communicate to the user having taken control of the target screen EC the location of the reserved space.

It should be noted that the fixed communication terminal TC could be of the (wireless) radio type.

The invention proposes a method enabling the opening of a communication session between a radio (communication) terminal MS (in this case, a person's mobile phone) and a fixed communication terminal TC (in this case, a modem), coupled to (or equipped with) at least one target screen EC.

In the following discussion it is assumed by way of example and not of limitation that modem TC is coupled to just one target screen EC. However, it could be coupled to several (at least two) target screens.

The method according to the invention is implemented when a person equipped with a mobile phone TC is momentarily placed in front of a target screen EC that displays general information containing at least one (potentially communication) identifier IC1, such as e.g. a telephone number (or else an Internet address, or similar), or a logo, or alternatively a cryptogram, enabling access to information, and that such person should wish to access at least some of the said items of information.

Figure 2:
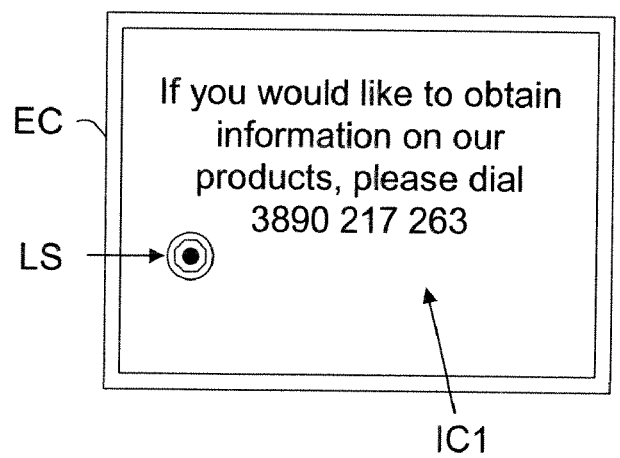

FIG. 2 schematically represents, by way of example but not of limitation, general information that could be displayed on a target screen EC. In this example, the message displayed invites the persons reading it to call the number 3890 217 263 in order to obtain information on the articles sold in the shop MA. It will be noted that in this example the identifier IC1 is a communication identifier accompanied by a logo (or symbol) LS that signals to the persons the affiliation to a service. However, this logo LS is not mandatory. A logo LS of this type can notably be useful if the communication identifier is not accompanied by a message. In that case, when a person sees the communication identifier and the logo (or symbol) LS, he/she immediately understands that this communication identifier enables access to information that will display on the target screen EC placed in front of him/her. The logo or a cryptogram can also be used as an identifier. It must then be captured by a photography application of the mobile phone MS.

The method comprises a first step during which a person sends, by means of his/her mobile phone MS, the identifier IC1, which is displayed on the target screen EC in front of which the person is momentarily positioned, in order to open a communication session between his/her mobile phone MS and the modem TC to which is coupled the EC target screen.

It will be noted that the communication identifier used may have been chosen from a list displayed on the target screen EC.

Besides, in the following discussion it is considered by way of example and not of limitation that the identifier IC1 that is used is a communication identifier. It is therefore dialed with the man/machine interface MI of the mobile phone MS. However, as indicated earlier, the identifier IC1 may be a logo or a cryptogram that must be captured by a photography application of the mobile phone MS, and then sent.

The method then comprises a second step in the course of which the display of information on the target screen EC is controlled by means of the mobile phone MS.

Preferably, such control takes place by means of transferring control of the display to the mobile phone MS.

Control of opening the communication session and of transferring control of the display can take place by means of a server SR that is connected to one of the networks R1 and R2, or else accessible to at least one of them. In the example—not intended to act as limitation—illustrated in FIG. 1, the server SR is connected to the mobile network R1. However, it could be connected to the wireline network R2.

It will be noted that such server SR may potentially take the shape of an application server installed in a core network, potentially of the IMS type.

It will be understood that a server SR of this nature can advantageously control the opening of communication sessions with several fixed communication terminals TC, as well as the transfer of control of the display of several target screens EC from each of those fixed communication terminals TC. Consequently, it may be envisaged that several different persons placed before different target screens EC, coupled to one and the same fixed communication terminal TC, may, in parallel, take control of the display on those different target screens EC if the said fixed communication terminal TC allows for this. It may also be envisaged that several different persons placed before one and the same target screen EC, coupled to a fixed communication terminal TC, may, in parallel, take control of the display of different portions of the said target screen EC if the said fixed communication terminal TC and the said target screen EC allow for this.

The (communication) identifier IC1, which is initially dialed (or sent) by means of the mobile phone MS, therefore addresses not only the server SR, but also a fixed communication terminal TC (in this case a modem), as well as potentially a target screen EC if the said modem TC is coupled to several target screens EC.

The server SR therefore takes charge of opening the communication session between the requesting mobile phone MS and the modem TC designated by the (communication) identifier IC1, then of transferring to the mobile phone MS the control of the display of information on the target screen EC (potentially designated by the said (communication) identifier IC1).

For example, consecutively to the transfer of the display control, a first set of predefined information can be automatically displayed on the target screen EC constituting the subject of the transfer.

Figure 3:
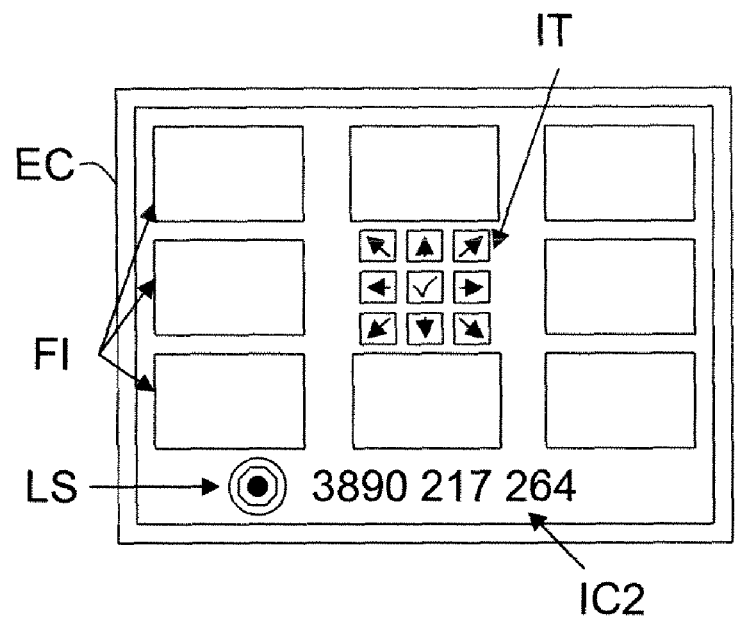

FIG. 3 schematically represents, by way of example but not of limitation, a first set of information displayed on a target screen EC. In this example, the first set of information is distributed among eight information windows FI and in icons IT symbolizing the keys to be activated by a person on his/her mobile phone MS to access the different information windows FI, and are accompanied by a second (potentially communication) identifier IC2 (3890 217 264) enabling access to other (potentially more detailed) information.

It shall be noted that the second identifier IC2 may also be a logo or a cryptogram that must be captured by a photography application of the mobile phone MS, and then sent.

For example:

the icon ↑ corresponds to the number 2 on the keypad of the mobile phone MS and enables selection of the window placed in the upper central position, the icon ↖ corresponds to the number 1 on the keypad of the mobile phone MS and enables selection of the window placed in the upper left position, the icon ↗ corresponds to the number 3 on the keypad of the mobile phone MS and enables selection of the window placed in the upper right position, the icon ← corresponds to the number 4 on the keypad of the mobile phone MS and enables selection of the window placed in the central left position, the icon → corresponds to the number 6 on the keypad of the mobile phone MS and enables selection of the window placed in the central right position, the icon ↓ corresponds to the number 8 on the keypad of the mobile phone MS and enables selection of the window placed in the lower central position, the icon ↙ corresponds to the number 7 on the keypad of the mobile phone MS and enables selection of the window placed in the lower left position, the icon ↘ corresponds to the number 9 on the keypad of the mobile phone MS and enables selection of the window placed in the lower right position, and the icon √, placed in the center, corresponds to the number 5 on the keypad of the mobile phone MS and (potentially) enables validation of the selection of a window.

It will be understood that the selection of a window brings about the display of information it contains on all or the greatest part of the target screen EC. This is equivalent to a zooming operation. It shall be noted that, by selecting a window, this may potentially cause the additional display on the target screen EC of a new identifier (potentially a communication identifier or a logo or cryptogram) ICn enabling access to additional or more detailed information and/or to a selection mask. The fact of activating a key on a mobile phone MS is therefore interpreted as being a navigation (or browsing) instruction by the server SR and transmitted to the modem TC, and then to the control logic of the target screen EC. This logic then chooses a content that may already be in the memory associated to the target screen EC or that is sent to the latter by the server SR.

It is important to note that the information intended to be displayed on the target screen EC may be stored in the storage means of the TC (MM1') and/or of the server SR (MM1) and/or of another network device (not represented on FIG. 1).

The content information displayed in the information windows FI is therefore:

either that sought by the person, and in that case the latter will read it and may request additional services provided by applications that may be triggered by the server SR (as for example a storage application in his/her mobile phone or in another communication device, or a connection application with another person or communications device, or else an application for notification of the interest manifested by the person for a potential follow-up by the organization having produced the content displayed), or used to continue searching for more detailed or different content. In this case, the person may, for example, dial (or send), by means of the man/machine interface MI of his/her mobile phone MS, the (communication) identifier IC2, which is displayed on the target screen EC in front of which the person is momentarily positioned. The fact of dialing (or sending) this new (communication) identifier IC2 is interpreted by the server SR as a request for access to information other than the first set of information displayed in the information windows FI. This is therefore also a navigation instruction that is potentially transmitted to the control logic of the target screen EC.

Figure 4:
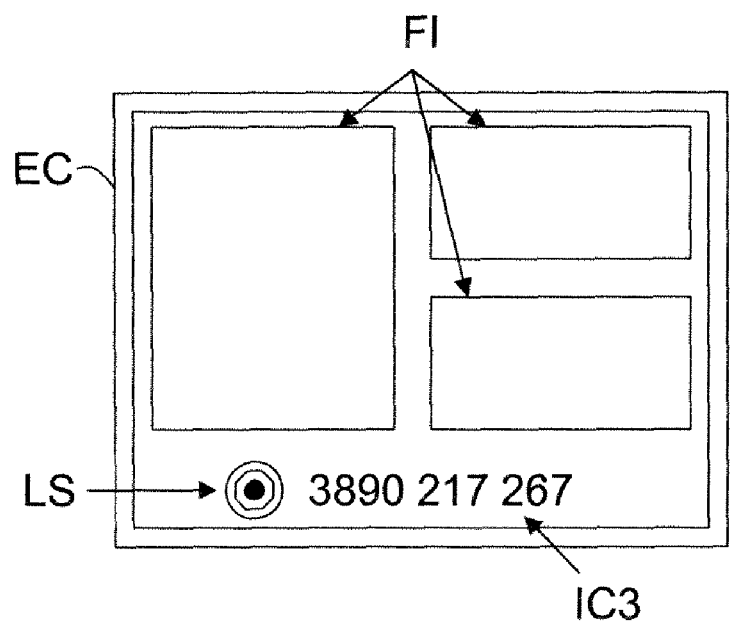

FIG. 4 schematically represents, by way of example but not of limitation, (three) information windows FI that are displayed on the target screen EC consecutively to the dialing (or sending) of a new (second) identifier (potentially a communication identifier or logo or cryptogram) IC2 (3890 217 264) displayed on a previous screen (in this case, that of FIG. 3). It will be noted that a new identifier (potentially a communication identifier or logo or cryptogram) IC3 (in this case, 3890 217 267) may potentially accompany the new information displayed on the target screen EC and enable access to yet other information (potentially more detailed).

If a person should wish to return to information previously displayed on the target screen EC, he/she may e.g. use the "back" key on his/her mobile phone MS, which is coupled to a memorization function for the latest actions carried out, and the command to display the previous information is then transmitted to the target screen EC. The methods that may be used for this return function are standard and well known by a person skilled in the art.

It will be understood that in the invention the mobile phone MS in some way constitutes a sophisticated communicating remote control.

It is important to note that the information displayed on a target screen EC is not necessarily static (text or image). The information in question can also consist of video images (potentially accompanied by a sound track (audio). The latter may be transmitted to the mobile phone MS by the server SR so that only the user can hear it, thus preventing it from being broadcast in the street or in a public place.

A communication session between a mobile phone MS and a modem TC may be terminated either upon the initiative of the person using the mobile phone MS, by activating a key of the man/machine interface MI dedicated to interruption of the communication, or else by detection of the absence of a display control operation generated by the mobile phone MS for a period greater than a chosen threshold (e.g. equal to 30 seconds or one minute). The latter case necessitates triggering a timeout every time a mobile phone MS transmits a signal consecutively to activation of a key of its man/machine interface MI. It is the server SR that may be in charge of terminating a communication session if it detects that the threshold has been exceeded (if it manages the pertinent timeout), or else interruption of the communication with the mobile phone MS.

It will be noted that it can be envisaged to transmit to the mobile phone MS at least some of the information displayed on the target screen EC whose display it controls in order for it to be displayed in parallel on its display screen EA, and/or additional information contained e.g. in audio messages. Of course, this requires the person using the mobile phone MS to activate at least one key on the phone's man/machine interface Ml that has been designated by information displayed on the target screen EC.

It will be noted that once a person has found the information that interests him/her and that is displayed on the target screen EC, a display message may prompt the person to store that information in storage means MM2 of the person's choice, e.g. that are comprised in his/her mobile phone MS or else in a desktop (or laptop) computer OF that is connected to a communication network, such as e.g. the wireline network R2 (as in the example—not constituting a limitation—shown in FIG. 1). It is the server SR that may be charged of controlling the transfer of information displayed to the designated storage means MM2.

It will equally be noted that takeover of display control may potentially be a paying service. Consequently, the invention may enable control of billing of display control to the subscriber to whom the telephone number of the mobile phone MS used in the process has been assigned. Such billing may concern the control takeover and/or the duration of the control and/or the amount of information displayed during a communication session and/or the quantity of information transmitted and/or the duration of its transmission to the mobile phone MS. In certain cases (e.g. that of a tourist), it is possible to buy a subscription so as to gain access that is (or is not) limited in time to a certain number of target screens EC located at predefined places of interest. Interaction with the target screens EC then provides access to video and/or audio and/or text information in the user's language. Billing may e.g. be controlled in the standard manner by the server SR, or else be handled by the time or volume billing mechanisms usually employed in mobile networks.

Some simple embodiments of the invention not given by way of limitation are described below.

A first embodiment corresponds to the situation illustrated in FIG. 1. In this case it is considered that the shop MA is a shoe shop. The person in front of the target screen EC dials (or sends) the (communication) identifier IC1 displayed on that target screen EC with his/her mobile phone MS. General information will then display on the target screen EC, and the person may browse that general information (in order to zoom) or else other information by dialing (or sending) another (communication) identifier IC2 displayed on the target screen EC with the general information. For example, it is possible to present to the person all the shoe models on sale in the shop MA, or else the person can be prompted to communicate his/her shoe size so that only those models for which the pertinent size is available will be presented. The person may then be prompted to select at least one of the shoe models presented in order to enable him/her to try them on inside the shop MA. Once the person has thus preselected the individual models, they can then quickly be presented to him/her once he/she enters the shop MA. It can also be envisaged to prompt the person to verify whether a selected model is available in another shop of the same chain.

A second embodiment corresponds to a situation in which a person who is at home watches the target screen EC of his/her TV set, which is connected to (or includes) a modem TC. For example, the program displayed comprises a (communication) identifier enabling access to information describing it or the persons or objects appearing in it. The person then dials (or sends) the said (communication) identifier with his/her mobile phone MS and general information will display on the target screen EC replacing the program or else superimposed or as a pop-up or overlay, and the person may potentially access other (potentially more detailed) information by dialing (or sending) another displayed (communication) identifier. The information displayed comes either from the television program broadcast network or from the Internet.

A third embodiment corresponds to a situation in which the person is situated in front of a target screen EC installed in a street, a building, a public transport vehicle, or a public place. The target screen displays a message proposing access to information about the place where the person is, or about a suggested service. The person then dials (or sends) the said (communication) identifier with his/her mobile phone MS and general information will display on the target screen EC. For example, one of the information windows displayed will prompt the person to choose a language. If the person is not from that country, with his/her mobile phone MS he/she will then select the language of his/her choice from a suggested list. The information will then display on the target screen EC in the selected language, and the person may potentially access other (potentially more detailed) information by dialing (or sending) another displayed (communication) identifier. It will be noted that video images may be displayed on the target screen EC, and that they may potentially be accompanied by a sound track in the selected language, which may be transmitted to the mobile phone MS to be broadcast over its speaker, thus avoiding inconvenience to the other persons situated in the proximity of the target screen EC.

The server SR is preferably embodied as a combination of electronic circuits (hardware) and of programming modules (software). However, it could also be embodied as electronic circuits, indeed even essentially software modules if integrated into a device (such as e.g. a network device or a fixed communication terminal).

The invention offers a certain number of benefits, including:
- a new type of service based on the localization (LBS) of radio communication terminals of any generation, not requiring adaptation or interfaces or localization,
- it grants access to a large number of applications,
- it does not require any knowledge or particular competence on the part of the persons using it,
- customized information, in particular as concerns the language of display and/or broadcast,
- mix, on a digital TV set (or screen) of contents to be broadcast (potentially by means of a video on demand, or VoD, service), e.g. of the following types: TV programs, with information and/or applications (such as e.g. games) desired by the user and transmitted e.g. via the Internet.

The invention is not limited to the embodiments of a server or to the method of opening a communication session as described above, but, rather, it encompasses all variants that a person skilled in the art may consider within the framework of the claims below.

Thus, the invention applies also to the provision of information concerning advertising displayed on target screens, as well as to the triggering of applications of the type of those presented earlier.

The invention claimed is:

1. A method for opening a communication session between a radio communication terminal (MS), connected to a radio communication network (R1) and a fixed communication terminal (TC), coupled to at least one target screen (EC) and connected to a communication network (R2), the method comprising sending, via the radio communication terminal (MS), an identifier displayed on the target screen (EC) to open a communication session between the radio communication terminal (MS) and the fixed communication terminal (TC) and to control the display of information on the target screen (EC) via the radio communication terminal (MS), wherein the target screen further comprises a first set of information distributed among a plurality of information windows and in icons symbolizing keys to be activated on the radio communication terminal to access the plurality of information windows.

2. The method according to claim 1, wherein the control of the display of information is transferred to the radio communication terminal (MS).

3. The method according to claim 2, further comprising: the radio communication terminal (MS) sending an identifier chosen from a list displayed on the target screen (EC) to a server (SR), the server (SR) opening the communication session, and using the server (SR) to transfer the display control.

4. The method according to claim 1, wherein in the presence of an identifier of the communication identifier type, the identifier is dialed via the radio communication terminal (MS).

5. The method according to claim 1, wherein an interface (MI) of the radio communication terminal (MS) is used to carry out operations enabling action on at least some of the information displayed on the target screen (EC) and/or to cause display on the target screen (EC) of certain stored information.

6. The method according to claim 1, wherein the event of display on the target screen (EC) of information accompanied by another identifier granting access to other stored information, display of such other stored information is caused by sending such other identifier with the radio terminal (MS).

7. The method according to claim 1, wherein display takes place on a display screen (EA) of the radio communication terminal (MS) of at least some of the information displayed on the target screen (EC).

8. The method according to claim 1, wherein (a) at least one of the telecommunications applications selected from a group comprising at least one application intended for connection of the user of the radio communication terminal (MS) with another user or a communication device, and (b) an application enabling storage of at least some of the information displayed on the target screen (EC) in a storage means (MM2) designated by the user of the radio communication terminal (MS), are triggered.

9. The method according to claim 1, wherein audio messages associated to the information displayed to enable them to be heard by their user are transmitted to the radio communication terminal.

10. The method according to claim 1, wherein the communication session will be terminated in the event of detection of an absence of display control operations with the radio communication terminal (MS) for a duration that is longer than a chosen threshold.

11. The method according to claim 1, wherein the communication session will be terminated if and when the user of the radio communication terminal (MS) interrupts the communication.

12. The method according to claim 1, wherein the communication session will be billed to the user of the radio communication terminal (MS) for the assumption of control of the display.

13. The method according to claim 1, wherein a radio fixed communication terminal (TC) stores at least some of the information intended to be displayed on the target screen (EC).

14. The method according to claim 3, wherein the server (SR) stores at least some of the information intended to be displayed on the target screen (EC).

15. A network and communication server (SG), that is equipped, in the event of establishing a communication with a radio communication terminal (MS) connected to a radio communication network (R1) to which is coupled, consecutively to transmission by the radio communication terminal (MS) of an identifier displayed on the target screen (EC) coupled to a fixed communication terminal (TC) connected to a communication network (R2), to open a communication session between the radio communication terminal (MS) and the fixed communication terminal (TC), then to transfer to the said radio communication terminal (MS) the control of the display of information on the target screen (EC), wherein the target screen further comprises a first set of information distributed among a plurality of information windows and in icons symbolizing keys to be activated on the radio communication terminal to access the plurality of information windows.

16. The server according to claim 15, wherein it is equipped, in the event of transmission by the radio communication terminal (MS) during the communication session of another identifier displayed on the target screen (EC) and granting access to other stored information, so as to authorize access to such other information stored in a manner such that it can be displayed on the target screen (EC).

17. The server according to claim 15, wherein it is equipped to authorize transmission to the radio communication terminal (MS) of at least some of the information displayed on the target screen (EC) with a view to their display on a display screen (EA) of the radio communication terminal (MS).

18. The server according to claim 15, wherein it is equipped to trigger (a) at least one of the telecommunications applications selected from a group comprising at least one application intended for connection of the user of the radio communication terminal (MS) with another user or a communication device, and (b) an application enabling storage of at least some of the information displayed on the target screen (EC) in the storage means (MM2) designated by the user of the radio communication terminal (MS).

19. The server according to claim 15, wherein it is equipped to transmit audio messages associated to the information displayed on the target screen (EC) to the radio communication terminal to enable them to be heard by their user.

20. The server according to claim 15, wherein it is equipped to terminate the communication session in the event of detection of an absence of display control operations with the radio communication terminal (MS) for a duration that is longer than a chosen threshold.

21. The server according to claim 15, wherein it is equipped to terminate the communication session if and when the user of the radio communication terminal (MS) interrupts the communication.

22. The server according to claim 15, wherein it is equipped to control billing to the user of the radio communication terminal (MS) for the assumption of control of the display.

23. The server according to claim 15, wherein it comprises storage means (MM1) storing at least some of the information intended to be displayed on the target screen (EC).

24. The server according to claim 15, wherein it is equipped to authorize transmission to an address designated by the user of the radio communication terminal (MS) of at least some of the information displayed on the target screen (EC) with a view to its display on a display screen (EA) of the radio storage in storage means (MM2).

25. The method according to claim 1, wherein the target screen further comprises a second identifier that enables access to additional stored information.

26. The method according to claim 1, wherein the target screen is configured to allow two or more persons located in front of the target screen, in parallel, to take control of the display of different portions of the target screen.

27. The method according to claim 3, wherein the server is operative to control the opening of communication sessions with a plurality of fixed communication terminals and transfer of control of the display of a plurality of target screens from each of the fixed communication terminals.

* * * * *